US00PP28162P3

(12) United States Plant Patent
Ren

(10) Patent No.: US PP28,162 P3
(45) Date of Patent: Jul. 4, 2017

(54) ***ECHINACEA* PLANT NAMED 'BALSOMBABUR'**

(50) Latin Name: *Echinacea×hybrida*
Varietal Denomination: Balsombabur

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 84 days.

(21) Appl. No.: 14/756,239

(22) Filed: Aug. 19, 2015

(65) Prior Publication Data

US 2017/0055426 P1 Feb. 23, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

U.S. PATENT DOCUMENTS 7,982,110 B2 * 7/2011 Ren ..... A01H 5/12 435/410

OTHER PUBLICATIONS

Loren C. Stephens, Self-incompatibility in *Echinacea purpurea,* HortScience 43(5): 1350-1354. 2008.*

* cited by examiner

*Primary Examiner* — Anne Grunberg
(74) *Attorney, Agent, or Firm* — Audrey Charles

(57) ABSTRACT

A new and distinct cultivar of *Echinacea* plant named 'Balsombabur', characterized by its deep burgundy-colored inflorescences, medium green-colored foliage, and moderately vigorous, compact-upright growth habit, is disclosed.

1 Drawing Sheet

Latin name of genus and species of plant claimed: *Echinacea×hybrida.*

Variety denomination: 'Balsombabur'.

BACKGROUND OF THE INVENTION

The present invention relates to a new and distinct cultivar of *Echinacea* plant botanically known as *Echinacea×hybrida* and hereinafter referred to by the cultivar name 'Balsombabur'.

The new cultivar originated in a controlled breeding program in Elburn, Ill. during October 2010. The objective of the breeding program was the development of *Echinacea* cultivars with a single inflorescence form having imbricate ray florets and a well-branched, compact growth habit.

The new *Echinacea* cultivar is the result of cross-pollination. The female (seed) parent of the new cultivar is the proprietary *Echinacea×hybrida* breeding selection coded E74-2, U.S. Pat. No. 7,982,110, characterized by its single-type, dark red colored ray florets having a light tip, medium green-colored foliage, and vigorous, upright growth habit. The male (pollen) parent of the new cultivar is from a bulk pollen mix of five proprietary *Echinacea×hybrida* breeding selections coded E74-1, E74-3, E74-4, E74-5, and E74-6, U.S. Pat. No. 7,982,110, characterized by their single-type, medium to dark shades of orange and red-orange colored ray florets, medium green-colored foliage, and vigorous, upright growth habits. The new cultivar was discovered and selected as a single flowering plant within the progeny of the above stated cross-pollination during September 2011 in a controlled environment in Elburn, Ill.

Asexual reproduction of the new cultivar by in vitro propagation since September 2011 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsombabur' as a new and distinct cultivar of *Echinacea* plant:

1. Deep burgundy-colored inflorescences;
2. Medium green-colored foliage; and
3. Moderately vigorous, compact-upright growth habit.

Plants of the new cultivar differ from plants of the female parent and the possible male parents primarily in ray floret color and in having a more branched habit.

Of the many commercially available *Echinacea* cultivars, the most similar in comparison to the new cultivar is SOMBRERO Salsa Red 'Balsomsed', U.S. Plant Pat. No. 23,105. However, in side by side comparisons, plants of the new cultivar differ from plants of 'Balsomsed' in at least the following characteristics:

1. Plants of the new cultivar are taller than plants of 'Balsomsed';
2. Plants of the new cultivar have larger leaves than plants of 'Balsomsed'; and 3. Plants of the new cultivar have a ray floret color different from plants of 'Balsomsed'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsombabur'. The plants were transplanted from one-gallon containers and grown in a garden-type bed for 3 months in West Chicago, Ill.

DETAILED BOTANICAL DESCRIPTION

Figure 1:
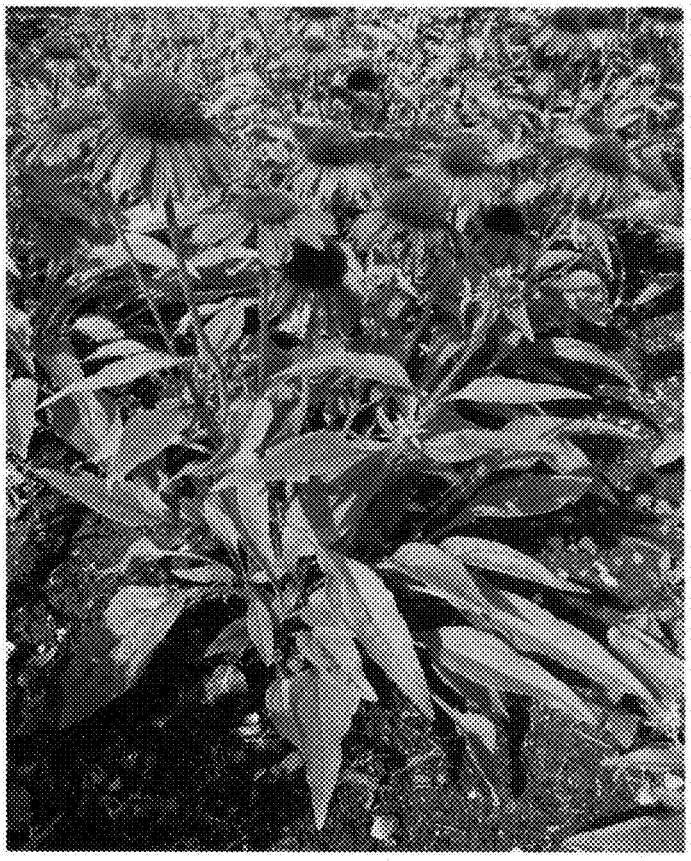
FIG. 1 illustrates a side view of the overall growth and flowering habit of 'Balsombabur'.
Figure 2:
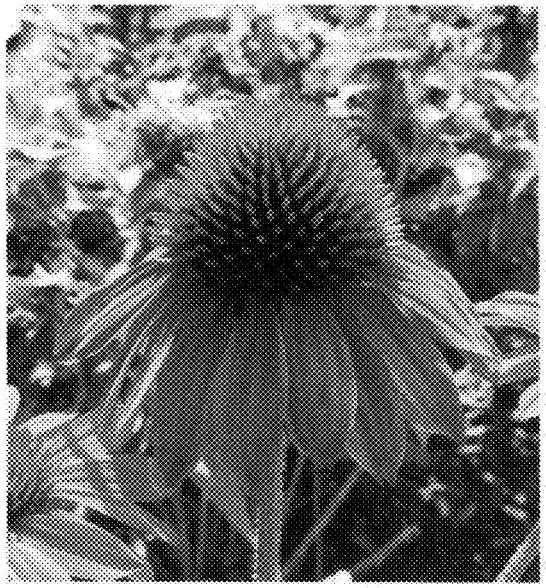
FIG. 2 illustrates a close-up view of an individual inflorescence of 'Balsombabur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2015 under natural light conditions in West Chicago, Ill.

The following descriptions and measurements describe plants produced from in vitro plantlets and grown under conditions comparable to those used in commercial practice. The plants were transplanted from one-gallon containers and grown in a garden-type bed for 3 months in West Chicago, Ill. During this period the temperature ranged from a low of 41° F. (5° C.) and a high of 93° F. (34° C.). Measurements and numerical values represent averages of typical plants.

Botanical classification: *Echinacea×hybrida* cultivar Balsombabur.

Parentage:

*Female parent*.—Proprietary *Echinacea×hybrida* breeding selection coded E74-2, U.S. Pat. No. 7,982,110.

*Male parent*.—Bulk pollen mix of five proprietary *Echinacea×hybrida* breeding selections coded E74-1, E74-3, E74-4, E74-5, and E74-6, U.S. Pat. No. 7,982,110.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 14 to 16 weeks from a rooted tissue culture plantlet to finish in a one-gallon container.

*Growth habit and general appearance*.—Compact-upright, herbaceous perennial.

*Growth rate*.—Moderately vigorous.

*Outdoor plant performance*.—Use as bedding plants or in mixed-container plantings; at least tolerant to temperatures up to 35° C. and hardy to USDA zone 4.

*Size*.—Height from soil level to top of plant plane: Approximately 47.5 cm. Width: Approximately 41.0 cm.

*Branching habit*.—No lateral branching, flowering stems grow from base. Quantity of main stems per plant: Approximately 4.

*Stems*.—Strength: Very strong. Aspect: Nearly erect. Shape: Rounded. Length to base of inflorescence: Approximately 20.0 cm. Diameter: Approximately 6.0 mm. Length of central internode: Approximately 3.0 cm. Texture: Densely pubescent with short strigose hairs. Color of young stems: 144A to 144B. Color of mature stems: 144A to 144B with an overlay of 187A.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, slightly undulate. Apex: Acute. Base: Attenuate. Venation pattern: Pinnate. Length of mature leaf: Approximately 14.5 cm. Width of mature leaf: Approximately 5.0 cm. Texture of upper surface: Dull, moderately pubescent with short strigose hairs. Texture of lower surface: Moderately pubescent with short strigose hairs. Color of upper surface of young and mature foliage: Closest to 137A with venation of 147C, midvein often has overlay of 187A. Color of lower surface of young and mature foliage: Closest to 147B with venation of 147D.

*Petiole*.—Shape: V-shaped. Length: Approximately 11.0 cm. Diameter: Approximately 3.0 mm. Texture of upper surface: Glabrous. Texture of lower surface: Sparsely covered with very short strigose hairs. Color of upper and lower surfaces: 147D with an overlay of 187A.

Flowering description:

*Flowering habit*.—'Balsombabur' is freely flowering under outdoor growing conditions blooming from spring through autumn and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 6. Height: Approximately 5.5 cm. Diameter: Approximately 6.5 cm.

*Peduncle*.—Strength: Strong. Aspect: Erect to approximately 45° from vertical. Length: Approximately 24.0 cm. Diameter: Approximately 5.0 mm. Texture: Densely pubescent with short strigose hairs. Color: 144A to 144B with an overlay of 187A.

*Bud*.—Quantity per plant: Approximately 3. Shape: Flattened globular with immature ray florets nearly erect. Length: Approximately 1.5 cm. Diameter:

Approximately 1.7 cm. Color: Outer ray florets of 154D with 187B at tip; bud center of 143A.

*Ray florets*.—Quantity per inflorescence: Approximately 19. Arrangement: In a single whorl, slightly imbricate. Aspect: Perpendicular to disc, subtending with age. Shape: Elliptic to narrowly obovate. Appearance: Dull. Margin: Entire. Apex: Emarginate to notched. Base: Attenuate. Length: Approximately 3.5 cm. Width: Approximately 1.3 cm. Texture of upper surface: Glabrous, ribbed longitudinally. Texture of lower surface: Sparsely pubescent, ribbed longitudinally. Color of upper surface when first open: 46B. Color of lower surface when first open: 70A. Color of upper surface when fully open: 53A changing to 59A to 59B with age. Color of lower surface when fully open: Close to 70A with tips of 145B; darkens slightly with age.

*Disc florets*.—Disc diameter: Approximately 3.5 cm. Quantity per inflorescence: Approximately 350. Arrangement: Spirally arranged in center of inflorescence. Shape: Tubular. Margin of free portion: Entire. Apex: Five acute tips. Base: Fused into a tube. Length: Approximately 9.0 mm. Diameter: Approximately 2.0 mm. Texture: Glabrous. Color of upper or inner surface when first and fully open: 145C with 185A at tips. Color of lower or outer surface when first and fully open: 145B transitioning to 145D at base and 185A at tips.

*Receptacle*.—Shape: Conical. Height: Approximately 1.9 cm. Diameter: Approximately 1.5 cm. Color: 155D.

*Phyllaries*.—Quantity per inflorescence Approximately 36. Arrangement: In a three whorls. Appearance: Dull, stiff. Shape: Narrowly ovate to lanceolate, strongly curved towards the peduncle. Margin: Entire. Apex: Acute. Base: Truncate. Length: Approximately 1.2 cm. Width: Approximately 2.0 to 3.0 mm. Texture of upper or inner surface: Glabrous. Texture of lower or outer surface: Moderately pubescent with short strigose hairs. Color of upper surface: 137A. Color of lower surface: 137B.

*Receptacle spines*.—Number of spines per disc: Approximately 350. Shape: Acicular. Length: Approximately 1.3 cm. Width at widest point: Approximately 2.0 mm. Apex: Acute. Base: Truncate. Texture: Glabrous. Color: Apex of 167B tipped with 187A, mid-section of 144A, and base of 145D.

*Reproductive organs*.—Androecium: Present on disc florets only. Stamen quantity: 5 per floret. Anther shape: Oblong, basifixed. Anther length: Approximately 3.0 mm. Anther color: Closest to 203B. Filament length: Approximately 2.0 mm. Filament color: 145D. Pollen amount: Moderate to abundant. Pollen color: 14A. Gynoecium: Present on disc florets only. Pistil quantity: 1 per floret. Pistil length: Approximately 9.0 mm. Stigma shape: Bifid. Stigma length: Approximately 2.0 mm. Stigma color: 187A. Style length: Approximately 5.0 mm. Style color: 145D. Ovary length: Approximately 3.0 mm. Ovary color: 145D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balsombabur', substantially as herein illustrated and described.

* * * * *